(12) United States Patent
Neef et al.

(10) Patent No.: US 9,664,701 B2
(45) Date of Patent: May 30, 2017

(54) SYSTEM FOR HANDLING SLIDES HAVING TWO COVERSLIPPER MODULES

(75) Inventors: Bernhard Neef, Nussloch (DE); Simon Keimer, Leimen (DE); Karl-Heinz Westerhoff, Eppingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 1038 days.

(21) Appl. No.: 13/469,657

(22) Filed: May 11, 2012

(65) Prior Publication Data

US 2012/0287261 A1 Nov. 15, 2012

(30) Foreign Application Priority Data

May 13, 2011 (DE) .................. 10 2011 050 344

(51) Int. Cl.
*H04N 5/253* (2006.01)
*G01N 35/00* (2006.01)
*G01N 35/02* (2006.01)

(52) U.S. Cl.
CPC ..... *G01N 35/00029* (2013.01); *G01N 35/026* (2013.01); *G01N 2035/00079* (2013.01); *G01N 2035/00138* (2013.01)

(58) Field of Classification Search
CPC ... G01N 35/00029; G01N 2035/00079; G01N 2035/00138; G01N 35/026
USPC ......................................................... 348/110
See application file for complete search history.

(56) References Cited

U.S. PATENT DOCUMENTS

| 5,671,288 A | 9/1997 | Wilhelm et al. |
| 6,052,224 A | 4/2000 | Richardson |
| 2004/0009098 A1* | 1/2004 | Torre-Bueno ............... 422/63 |
| 2005/0250211 A1* | 11/2005 | Reinhardt et al. ........... 436/43 |
| 2012/0134893 A1 | 5/2012 | Neef |
| 2012/0134894 A1 | 5/2012 | Neef et al. |

FOREIGN PATENT DOCUMENTS

| CA | 2482441 A1 | 10/2003 |
| EP | 01 118 265 A1 | 9/1984 |
| EP | 2 239 554 A1 | 10/2010 |
| GB | 2485871 A | 5/2012 |
| WO | 2011/002779 A2 | 1/2011 |

OTHER PUBLICATIONS

United Kingdom Intellectual Property Office, Combined Search and Examination Report under Sections 17 and 18(3) issued in British counterpart application GB1207633.7, dated Aug. 16, 2012.

\* cited by examiner

*Primary Examiner* — Joseph Ustaris
*Assistant Examiner* — Jill Sechser
(74) *Attorney, Agent, or Firm* — Hodgson Russ LLP

(57) ABSTRACT

The present invention relates to a system (10) for handling slides, including a first and at least a second module-receiving area (24 through 28) for receiving at least one module (30, 34) for handling slides each. The first module-receiving area (24) accommodates a coverslipper module (30, 32) for coverslipping thin sections on slides with a mounting medium and a cover slip (48).

18 Claims, 1 Drawing Sheet

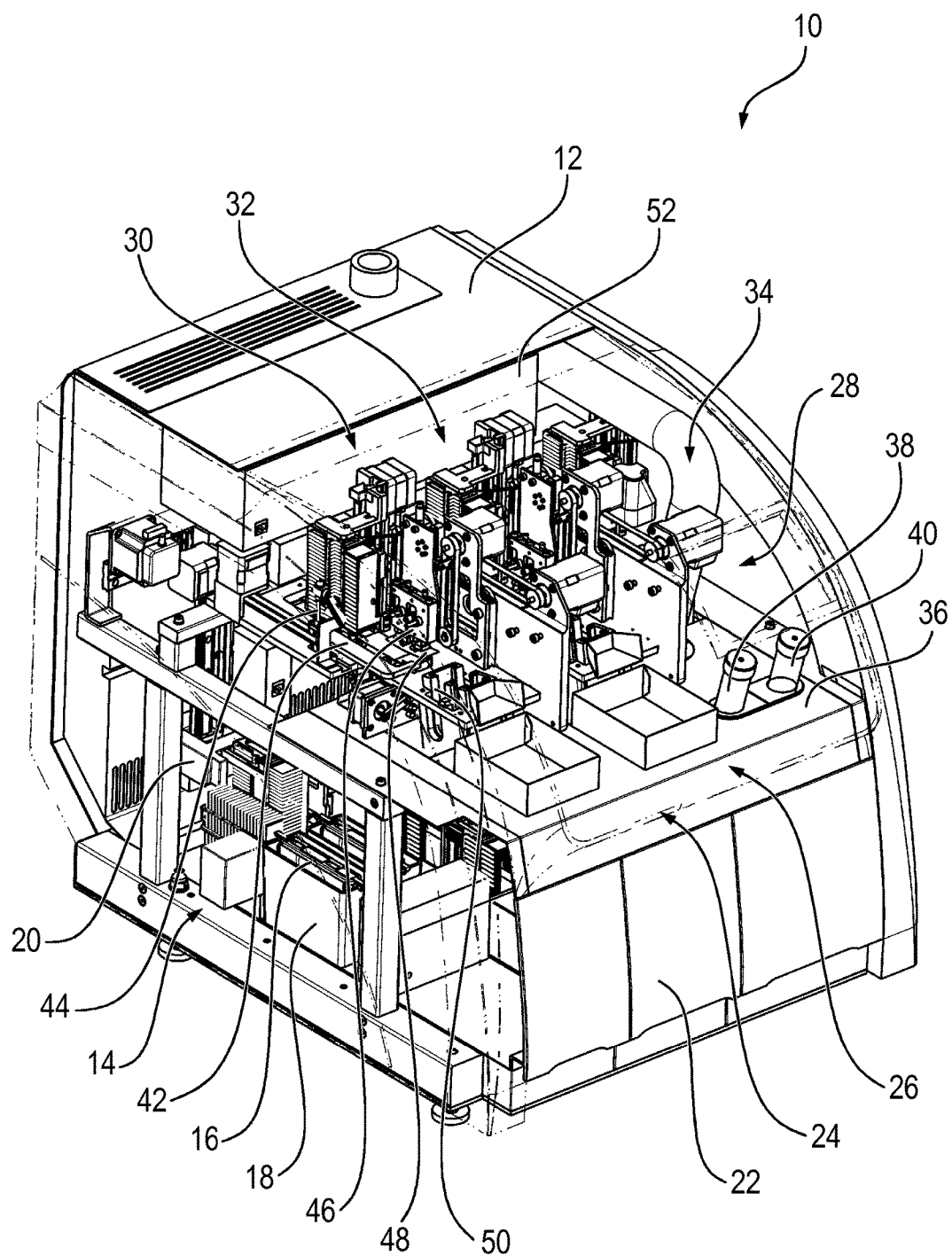

SYSTEM FOR HANDLING SLIDES HAVING TWO COVERSLIPPER MODULES

CROSS REFERENCE TO RELATED APPLICATIONS

This application claims priority of German patent application number 10 2011 050 344.7 filed May 13, 2011, the entire disclosure of which is incorporated by reference herein.

FIELD OF THE INVENTION

The present invention relates to a system for handling slides, including a coverslipper module for coverslipping thin sections on the slides with a mounting medium and a cover slip.

BACKGROUND OF THE INVENTION

In histology, thin sections obtained from tissue samples are placed on sample carriers referred to as slides. In order to prepare the slides for microscopy, the thin sections placed on the slides are typically treated, in particular dehydrated and/or stained. To protect the thin sections, a cover slip is placed on top. Prior to placement of the cover slip, a mounting medium is applied via which the cover slip adheres to the slide. After checking the coverslipping quality, the slides carrying the coverslipped thin sections are transferred to a microscope for further examination of the thin sections.

The coverslipping of the thin sections; i.e., the application of the mounting medium and the cover slip, is performed, in particular, using so-called automated coverslippers. Known coverslippers have a coverslipper module for applying a mounting medium received in a mounting medium reservoir and for subsequently applying cover slips received in a coverslip container. The treatment of the thin sections prior to coverslipping, and the further handling of the slides after the coverslipping, such as quality checking, are performed by separate devices. These separate upstream and downstream devices may be connected to the coverslipper via respective transfer interfaces, allowing the slides to be transferred automatically. The problem here is that a plurality of transfer interfaces are needed which, on the one hand, requires much space and, on the other hand, results in high susceptibility to faults. Alternatively, the slides may also be manually transferred to or removed from the coverslippers. However, the handling requires a lot of manpower and, in addition, is susceptible to faults.

Moreover, the known coverslippers are problematic because when slides are to be coverslipped with different mounting media or cover slips, the mounting medium reservoir and/or the coverslip container has/have to be emptied and filled with the new mounting medium or the new cover slips, respectively. In this case, the mounting medium reservoir and the mounting medium pump must be intensively cleaned, which requires very much effort. As a result, coverslipping operations in which mounting media and cover slips other than the standard ones are used are often performed manually to avoid this effort. This, on the one hand, is very laborious and, on the other hand, is susceptible to faults.

SUMMARY OF THE INVENTION

It is an object of the present invention to provide a system for handling slides that allows thin sections on slides to be coverslipped in a simple manner.

This object is achieved by a system having the features described herein. Advantageous embodiments of the present invention are described in the present specification.

In accordance with the present invention, the system has a first module-receiving area and a second module-receiving area for receiving at least one module for handling slides each. The coverslipper module for coverslipping thin sections placed on slides is received in the first module-receiving area. The second module-receiving area allows an additional module for handling slides to be accommodated in the same system, so that process steps to be performed successively during the preparation of thin sections for microscopy can be carried out in one single system without the need to transfer the slides between different separate systems. Alternatively, it is possible to increase the throughput of the system per unit time by providing identical modules in the two module-receiving areas. In particular, the provision of two such module-receiving areas allows the system to be configured very flexibility to meet the specific requirements of the operator of the system. The modular design in particular allows the modules to be quickly and easily replaced and adapted to individual requirements.

The system has, in particular, a housing which accommodates the two module-receiving areas.

The module-receiving areas each have, in particular, holding units provided therein to which may be attached the different modules that may be inserted into the module-receiving areas. Specifically, each module-receiving area includes a bottom plate having cutouts provided at predetermined positions, allowing the modules, or individual components of the modules, to be mounted therein and/or to be passed therethrough. In particular, each module-receiving area has at least one, preferably a plurality of interfaces for integrating a module into the system.

Furthermore, it is advantageous for the system to include an input compartment for receiving racks holding the slides, a transport unit for transporting racks, and a control unit for controlling the transport unit. Racks which are introduced via the input compartment can be transported by the transport unit from the input compartment directly to the first module-receiving area and directly to the second module-receiving area. Thus, the racks may be transferred to both the coverslipper module received in the first module-receiving area and to a module received in the second module-receiving area. Direct and immediate transfer means, in particular, that the racks need not be previously transferred to another module-receiving area. Thus, the modules received in the two module-receiving areas may be operated in parallel without the need to synchronize the two modules to each other.

In a particularly preferred embodiment, the coverslipper module received in the first module-receiving area is a first coverslipper module. In the second module-receiving area there is disposed, as the module for handling slides, a second coverslipper module for coverslipping thin sections on slides with a mounting medium and a cover slip. Thus, there are provided two coverslipper modules which may be operated in parallel, thereby increasing the throughput; i.e., the number of thin sections that can be coverslipped per unit time.

In an alternative embodiment, a quality control module for checking the quality of thin sections placed on the slides and/or the coverslipping quality may be disposed in the second module-receiving area in place of a second coverslipper module as the module for handling slides. In this case, the coverslipper module received in the first module-receiving area and the quality control module are operated, in particular, such that once the slides have been coverslipped by the coverslipper module, they are transported by the transport unit to the quality control module, so that the coverslipping quality and/or the quality of the thin sections can be checked in a simple manner. The integration of both the coverslipper module and the quality control module into one single system eliminates the need for a transfer interface and/or the need to manually transfer the slide between a device for coverslipping and a device for controlling quality.

The quality control module includes, in particular, a camera which captures at least one image showing at least a portion of the slide where the thin section is located. In a control unit, at least one image-processing algorithm is executed, said algorithm allowing the coverslipping quality and/or the quality of thin sections placed on the slides to be determined based on the image. This includes, in particular, detecting the staining quality of the thin section, mechanical damage to the thin section and/or to the cover slip, the relative position of the thin section on the slide and/or air inclusions between the slide and the cover slip. To this end, in particular, the captured image is compared to predetermined target values. If the comparison shows that the quality does not meet the predetermined requirements, then, in particular, an error message is issued to a user and/or data containing such an error message is stored uniquely for the particular rack in a database. The control unit for controlling the transport unit and the control unit for executing the image-processing algorithms are, in particular, identical. Alternatively, it is also possible to use different control units.

The control unit controls the transport unit in particular in such a way that once the slides have been coverslipped by the coverslipper module received in the first module-receiving area, the transport unit transports a rack containing these slides from the first module-receiving area to the second module-receiving area, so that the slides may be first processed by the module received in the first module-receiving area and then by the module received in the second module-receiving area. Alternatively, the transport unit may also be controlled in such a way that it transfers the rack with the slides first to the second module-receiving area and then to the first module-receiving area, so that the thin sections are first processed by the module received in the second module-receiving area and then by the module received in the first module-receiving area.

Furthermore, it is advantageous to provide a first mounting medium reservoir for storing a first mounting medium and a second mounting medium reservoir for storing a second mounting medium. The first mounting medium reservoir is connected to the first coverslipper module received in the first module-receiving area, so that the first mounting medium can be applied to slides via the first coverslipper module. The second mounting medium reservoir is connected to a second coverslipper module received in the second module-receiving area, so that the second mounting medium can be applied to slides via this second coverslipper module. The first mounting medium and the second mounting medium are, in particular, different, so that by providing two coverslipper modules which each have a separate mounting medium reservoir associated therewith, the thin sections can be coverslipped alternatively with one of the two mounting media using only one system. Thus, unlike known coverslippers, the mounting medium reservoir does not need to be emptied, cleaned and filled with the second mounting medium in order to switch from the first mounting medium to the second mounting medium. Thus, in particular, thin sections to be coverslipped with the first mounting medium as well as thin sections to be coverslipped with the second mounting medium may be introduced in any desired order without having to modify the configuration of the system.

Alternatively, both mounting medium reservoirs may contain the same mounting medium. In this case, a higher throughput is possible; i.e., a greater number of thin sections can be coverslipped per unit time as compared to a coverslipper that has only one coverslipper module.

Furthermore, it is advantageous to provide a first coverslip container for storing cover slips and a second coverslip container for storing cover slips. The first coverslip container is associated with the first module-receiving area, and thus with the first coverslipper module, so that it contains the cover slips that are applied by the first coverslipper module to the thin sections to be coverslipped by it. Analogously, the second coverslip container is associated with the second module-receiving area, and thus with a second coverslipper module that may be disposed therein, so that the second coverslipper module can apply the cover slips from the second coverslip container to the thin sections to be coverslipped by the second coverslipper module. In particular, the two coverslip containers may, in turn, contain different types of cover slips.

In a particularly preferred embodiment, a third module-receiving area is provided for receiving a further module for handling slides. This third module-receiving area is preferably also disposed parallel to the two other module-receiving areas, so that the rack introduced via the input compartment may be transported by the transport unit directly to the third module-receiving area, or from one of the other module-receiving areas to the third module-receiving area.

Disposed in the third module-receiving area is, in particular, a quality control module for checking the quality of the thin sections placed on the slides and/or the coverslipping quality, while a second coverslipper module is received in the second module-receiving area. Thus, there are provided two coverslipper modules and one quality control module; the two coverslipper modules operating in particular independently of each other, and the slides coverslipped by the first coverslipper module as well as those coverslipped by the second coverslipper module are transferable to the quality control module after drying. The quality control module is preferably designed as described above for a quality control module received in the second module-receiving area.

Thus, only one quality control module is needed for the two coverslipper modules, which results in a particularly simple and cost-effective design. Since all three modules are integrated within one system, a great number of thin sections can be coverslipped in a short period of time, while requiring a minimum number of transfers of slides, thus ensuring safe and reliable handling. In an alternative embodiment of the present invention, the first coverslipper module may be disposed in the first module-receiving area, and a quality control module may be disposed in each of the second and third module-receiving areas.

The transport device is in particular designed to allow racks, in which the slides are held, to be transported between all three module-receiving areas in any desired sequence without having to be moved to an additional module-receiving area during transport from one module-receiving area to another module-receiving area. Thus, all modules received in the module-receiving areas may be operated independently of each other, thereby enabling versatile use.

The system preferably includes a drying unit capable of removing the moisture of the mounting medium from both the slides that are coverslipped by the first coverslipper module and from those which are coverslipped by the second coverslipper module. This allows the mounting medium to dry faster than in the case of passive drying without a drying unit, thus preventing displacement of the cover slips. This in turn prevents damage to the thin sections and injury to the user.

Furthermore, the system preferably has an output compartment for outputting racks. The output compartment may be integrated with the drying unit to form one unit and, in particular, takes the form of a movable drawer, so that the finished coverslipped slides can be easily removed by the user.

Moreover, it is advantageous to provide a reader unit for reading information from an information carrier attached to the rack which is introduced via the input compartment. The control unit determines, based on the information read, which of the modules received in the module-receiving areas the rack is to be transported to and/or the order in which the rack is to be transferred to at least two of the module-receiving areas. The information includes, in particular, information indicative of the mounting medium and/or the type of cover slips with which the slides received in the rack are to be coverslipped. Based on this information, the control unit can decide whether the rack is to be transferred to the first or to the second coverslipper module.

The information carrier is, in particular, in the form a bar code or an RFID chip allowing the rack to be uniquely identified. Information uniquely associated with each rack, including, in particular, information indicative of the mounting medium to be used, is stored in a database. Based on the identification of a rack obtained from the information carrier, the control unit reads out the data that is associated with this rack in the database, and thus controls the transport unit in such a manner that it transfers the rack to the correct coverslipper module. Moreover, in addition to the type of mounting medium, the amount of mounting medium to be applied may, in particular, also be stored in the database.

The system is, in particular, designed with two levels, the first level accommodating the input compartment, the reader unit, the drying unit and/or the output compartment, and the second level accommodating the module-receiving areas. When the system is in its normal operating orientation, the two levels are in particular located one above the other, the first level being the lower level and the second level being the upper level. Thus, the lower level accommodates the units that are associated with all module-receiving areas, whereas the units located in the upper level may be operated independently of each other. The units located in the lower level are provided, in particular, to serve the modules located in the upper level. Since the module-receiving areas are located in the upper level, they are readily accessible, thus allowing easy replacement of the modules.

BRIEF DESCRIPTION OF THE DRAWING VIEW

Further features and advantages will become apparent from the following more detailed description of exemplary embodiments thereof, taken in conjunction with the accompanying drawing, in which:

The FIGURE is a schematic perspective view of an automated coverslipper.

DETAILED DESCRIPTION OF THE INVENTION

The FIGURE shows in schematic perspective form a system for handling slides which takes the form of a coverslipper 10. Housing 12 of coverslipper 10 is partially indicated by the dot-dash lines, so that the components located in and protected by housing 12 may be seen.

Coverslipper 10 includes an input compartment 14 via which racks 16 can be introduced into coverslipper 10. Located in racks 16 are slides having thin sections placed thereon which are to be coverslipped by coverslipper 10.

The slides may be introduced both manually and mechanically. This allows for both a stand-alone mode of operation, in which coverslipper 10 is not connected to other systems, and for a workstation mode of operation. In the workstation mode of operation, coverslipper 10 is disposed in particular adjacent to an automated stainer, so that once the thin sections placed on the slides have been stained, the slides are automatically received into racks 16 transferred from the stainer to coverslipper 10.

The racks 16 introduced via input compartment 14 are received in containers filled with xylene and held therein until they are further processed, one of said containers being denoted, by way of example, by reference numeral 18. Coverslipper 10 further has a transport unit 20 capable of transporting racks 16 within coverslipper 10. This transport unit 20 is designed to be capable of carrying out all transport operations of racks 16 within coverslipper 10 that are necessary to coverslip the slides. In particular, only one single transport unit 20 is needed to perform all transport operations of racks 16, from the introduction via input compartment 14 to the output via an output compartment 22.

Coverslipper 10 has three module-receiving areas 24 through 28 for receiving one module for handling slides each. In the exemplary embodiment shown in the FIGURE, each of the first and second module-receiving areas 24, 26 has disposed therein a coverslipper module 30, 32 for coverslipping thin sections placed on slides. Third module-receiving area 28 has a quality control module 34 placed therein.

In an alternative embodiment of the present invention, only one of module-receiving areas 24 through 28 may have a coverslipper module 30, 32 disposed therein, and the other two module-receiving areas may each accommodate a quality control module 34. Alternatively, it is also possible that one of module-receiving areas 24 through 28 is vacant; i.e., that no module 30 through 34 is received therein. In this case, in particular, a coverslipper module 30, 32 is received in one of the other two module-receiving areas 24 through 28, while the other one accommodates a quality control module 34. In another alternative embodiment of the present invention, only one of module-receiving areas 24 through 28 may have a coverslipper module 30, 32 disposed therein, and the other two module-receiving areas 24 through 28 may not have any module 30 through 34 placed therein.

Module-receiving areas 24 through 28 are bounded, in particular, by a support plate 36 to which modules 30 through 34 can be attached in a simple manner. In particular, modules 30 through 34, or individual components thereof, may be screwed to this support plate 36 in a simple manner, so that modules 30 through 34 can be easily replaced. Because of this, the set of modules 30 through 34 with which coverslipper 10 is equipped may be easily adapted to the individual requirements of the operator of coverslipper 10. Support plate 36 is in particular provided with a plurality of cutouts through which parts of modules 30 through 34 may extend.

Coverslipper 10 further includes two mounting medium reservoirs, which are not visible in the FIGURE. A first one of these mounting medium reservoirs is connected to first coverslipper module 30 while the second mounting medium reservoir is connected to second coverslipper module 32. The two mounting medium reservoirs can be filled with mounting media independently of each other via the two inlet ports 38, 40. The first mounting medium received in the first mounting medium reservoir is pumped to first coverslipper module 30, in particular by means of a first pump (not visible). Analogously, the second mounting medium received in the second mounting medium reservoir is pumped to second coverslipper module 32 by a second pump.

In the exemplary embodiment shown in the FIGURE, the two coverslipper modules 30, 32 are identical in design. Therefore, the explanations given below by way of example for first coverslipper module 30 apply analogously to second coverslipper module 32. In an alternative embodiment, the two coverslipper modules 30, 32 may be designed differently.

First coverslipper module 30 includes a removal unit 42 by means of which the slides in the rack 16 that has been introduced into first coverslipper module 30 are removed one after the other from this rack 16. Subsequently, a predetermined amount of the first mounting medium is applied to the slide in the region of the thin section using a hollow needle 44. Then, a suction cup device 46 removes a cover slip 48 from a coverslip container 50 and covers the thin section with this cover slip 48. After the slide is covered, it is transported back into rack 16 by removal unit 42. More specifically, the slide is transported into the same holding compartment in which it was held previously. Then, rack 16 is displaced to a position where removal unit 42 can remove another slide therefrom for coverslipping.

By providing two mounting medium reservoirs, the two coverslipper modules 30, 32 can be operated independently of each other; i.e., one coverslipper module 30, 32 can coverslip slides simultaneously with the other coverslipper module 30, 32. This makes it possible, in particular, to store two different mounting media in the two mounting medium reservoirs, so that, unlike the known coverslippers which have only one coverslipper module 30, 32, there is no need to change the mounting medium when different mounting media are required depending on the type of thin section.

Input compartment 14 includes a reader unit capable of reading information from an information carrier attached to rack 16, such as, for example, a bar code or an RFID chip. This information includes, in particular, information for uniquely identifying rack 16. Based on the information read from the information carrier, a control unit 52 of coverslipper 10 determines the mounting medium with which the slides received in this rack 16 are to be coverslipped. Accordingly, control unit 52 then controls transport unit 20 to transport rack 16 to the coverslipper module 30, 32 that contains the right mounting medium. Thus, the assignment of racks 16 to the two coverslipper modules 30, 32 operating in parallel can be accomplished automatically without having to make a manual selection. Control unit 52 has stored therein, in particular, a database in which the mounting medium to be used for a particular rack 16 is stored uniquely for each rack. Based on the information read, control unit 52 may uniquely identify rack 16, and thus read information from the database as to which mounting medium is to be used.

In an alternative embodiment, the information stored on the information carriers of racks 16 may already include the information as to which mounting medium is to be used. In this case, there is no need to store such a database in control unit 52.

Transport unit 20 is designed, in particular, as a linear transport mechanism having three linear axes oriented orthogonal to one another, so that it is capable of carrying out all transports within coverslipper 10. Thus, transport unit 20 is, in particular, able to move from input compartment 14 directly to any of module-receiving areas 24 through 28, so that it can transfer rack 16 directly to one of module-receiving areas 24 through 28 without having to previously transfer it to any of the other module-receiving areas 24 through 28. This ensures that modules 30 through 34 received in module-receiving areas 24 through 28 can be operated completely independently of each other.

Once all slides of a rack 16 received in one of coverslipper modules 30, 32 have been coverslipped, transport unit 20 removes this rack 16 from coverslipper module 30, 32 and transfers it to a drying unit, which is not visible in the FIGURE. The drying unit removes moisture from the mounting medium, so that the mounting medium dries up faster and the cover slip adheres securely to the slide and cannot be displaced during further handling of the slides. The drying unit includes, in particular, a drying chamber in which a plurality of racks 16 can be received at the same time and through which is passed a stream of air heated to a predetermined temperature by a heating element, so that the slides located in the air stream are reliably, quickly and gently dried.

After drying, transport unit 20 removes rack 16 from the drying unit and transfers it to quality control module 34, which is received in third module-receiving area 28. This quality control module 34 includes a camera which captures at least one image showing at least the coverslipped thin section of each slide. The coverslipping quality is determined based on this image. In particular, control unit 52 has image-processing algorithms stored therein, which are executed by the control unit and which make it possible to detect damage to the thin sections, cover slips and/or to the slides, air inclusions between the cover slip and the slide and/or improper staining of the thin sections. If quality control module 34 should detect that the coverslipping quality of a slide does not meet the specified minimum requirements, it outputs, in particular, information indicative of this condition to the user of coverslipper 10.

Once quality control module 34 has checked the coverslipping quality of all the slides received in rack 16, transport unit 20 transports rack 16 and the slides received back therein into output compartment 22, so that it can be removed by a user. Alternatively, removal can be performed automatically. Output compartment 22 is configured, in particular, in the manner of a drawer, which allows for easy removal of racks 16.

In an alternative embodiment of the present invention, the drying unit may be omitted. In this case, after racks 16 have been coverslipped by coverslipper modules 30, 32, they are transferred directly to quality control module 34.

The three module-receiving areas 24 through 28 are arranged, in particular parallel to one another, in an upper plane which, apart from them, accommodates only control unit 52. In contrast, input compartment 14, output compartment 22 and the drying unit are disposed in a lower level under this upper level, so that, on the one hand, a particularly compact design is achieved and, on the other hand, it is ensured that module-receiving areas 28 through 28 located above are easily accessible, so that modules 30 through 34 can be easily replaced.

LIST OF REFERENCE NUMERALS 10 coverslipper
12 housing 14 input compartment
16 rack
18 xylene container
20 transport unit
22 output compartment
24, 26, 28 module-receiving area
30, 32 coverslipper module
34 quality control module
36 support plate
38, 40 inlet port
42 removal unit
44 hollow needle
46 suction cup device
48 cover slip
50 coverslip container
52 control unit

What is claimed is:

1. A system for handling slides, comprising:
a housing (12) accommodating an upper level and a lower level below the upper level;
a first module-receiving area (24) disposed in the upper level within the housing (12);
a coverslipper module (30) for coverslipping thin sections on slides with a mounting medium and a cover slip (48), the coverslipper module (30) being disposed in the first module-receiving area (24), wherein the coverslipper module (30) has a first part and a second part;
at least one second module-receiving area (26) disposed in the upper level within the housing (12);
at least one module (32, 34) for handling slides, the at least one module being disposed in the at least one second module-receiving area (26), wherein the at least one module (32, 34) for handling slides has a first part and a second part;
a support plate (36) attached to the coverslipper module (30) and the at least one module (32, 34), wherein the support plate (36) has surfaces that define a plurality of cutouts through which the second part of the coverslipper module (30) and the second part of the at least one module (32, 34) for handling slides are configured to extend, and wherein the first part of the coverslipper module (30) and the first part of the at least one module (32, 34) for handling slides are engaged to the support plate (36) adjacent to one of the cutouts;
a plurality of units (14, 22) disposed in the lower level, each of the plurality of units being used commonly by the coverslipper module (30) and the at least one module (32, 34) for handling slides;
an input compartment (14) for receiving racks (16) holding the slides, the input compartment being one of the plurality of units disposed in the lower level;
a reader unit arranged to read information from an information carrier attached to a rack (16) received by the input compartment (14), the reader unit being one of the plurality of units disposed in the lower level;
a drying unit for removing moisture of the mounting medium from slides coverslipped by the first coverslipper module (30), the drying unit being one of the plurality of units disposed in the lower level;
an output compartment (22) for receiving racks (16) to be outputted from the system (10), the output compartment (22) being one of the plurality of units disposed in the lower level;
a transport unit (20) for transporting racks (16); and
a control unit (52) for controlling the transport unit (20);
wherein the transport unit (20) is operable to transport racks (16) received by the input compartment (14) from the input compartment (14) directly to the coverslipper module (30) disposed in the first module-receiving area (24); and
wherein the transport unit (20) is further operable to transport racks (16) received by the input compartment (14) from the input compartment (14) directly to the at least one module (32, 34) for handling slides disposed in the second module-receiving area (26).

2. The system (10) as recited in claim 1,
wherein the coverslipper module (30) is a first coverslipper module; and
wherein the module (32, 34) for handling slides is a second coverslipper module (32) for coverslipping thin sections on slides with a mounting medium and a cover slip (48).

3. The system (10) as recited in claim 1,
wherein the module (32, 34) for handling slides is a quality control module (34) for checking the quality of thin sections placed on the slides and/or the coverslipping quality.

4. The system (10) as recited in claim 3, wherein the quality control module (34) includes a camera which captures at least one image showing at least a portion of the slide where the thin section is located.

5. The system (10) as recited in claim 4,
wherein the control unit (52) executes at least one stored image-processing algorithm; and
at least one of a staining quality of the thin section, mechanical damage to the thin section and/or to the cover slip (48), a relative position of the thin section on the slide, and air inclusions between the slide and the cover slip (48) are detected by the control unit (52) based on the captured image with the aid of the image-processing algorithm.

6. The system (10) as recited in claim 1,
wherein the control unit (52) is configured to control the transport unit (20) such that once the slides in a rack (16) have been coverslipped by the coverslipper module (30) received in the first module-receiving area (24), the transport unit (20) transports the rack (16) containing these slides from the first module-receiving area (24) to the second module-receiving area (26).

7. The system (10) as recited in claim 6, wherein the control unit (52) is configured to control the transport unit (20) such that once the slides have been processed by the at least one module (32, 34) for handling slides received in the second module-receiving area (26), the transport unit transports the rack (16) containing these slides from the second module-receiving area (26) to the first module-receiving area (24).

8. The system (10) as recited in claim 2, comprising:
a first mounting medium reservoir for storing a first mounting medium to be applied to slides by the first coverslipper module (30); and
a second mounting medium reservoir for storing a second mounting medium to be applied to slides by the second coverslipper module (32).

9. The system (10) as recited in claim 2, comprising:
a first coverslip container (50) for storing cover slips (48) to be applied to slides by the first coverslipper module (30); and
a second coverslip container for storing cover slips which may be applied to slides by the second coverslipper module (32).

10. The system (10) as recited in claim 1, comprising:
a third module-receiving area (28); and
a further module (32, 34) for handling slides received by the third module-receiving area (28).

11. The system (10) as recited in claim 10,
wherein the coverslipper module (30) is a first coverslipper module;
wherein the module (32, 34) for handling slides is a second coverslipper module (32) for coverslipping thin sections on slides with a mounting medium and a cover slip (48); and
wherein the further module for handling slides is a quality control module (34) for checking the quality of thin sections placed on the slides and/or the coverslipping quality.

12. The system (10) as recited in claim 10,
wherein the transport unit (20) is operable to transport racks (16) directly between the input compartment (14) and the third module-receiving area (28), directly between the first module-receiving area (24) and the third module-receiving area (28) and directly between the second module-receiving area (26) and the third module-receiving area (28).

13. The system (10) as recited in claim 2, wherein the drying unit is configured for removing moisture of the mounting medium from slides coverslipped by the first coverslipper module (30) and from slides coverslipped by the second coverslipper module (32).

14. The system (10) as recited in claim 10, wherein the control unit (52) determines, based on the information read, which of the modules (30 through 34) received in the first through third module-receiving areas (24 through 28) the rack (16) is to be transported to by the transport unit (20).

15. The system (10) as recited in claim 14, wherein the control unit (52) further determines, based on the information read, an order in which the rack (16) is to be successively transferred to at least two of the modules (30 through 34) received in the first through third module-receiving areas (24 through 28).

16. The system (10) as recited in claim 10, wherein the first through third module-receiving areas (24 through 28) are disposed in the upper level.

17. The system (10) as recited in claim 1, wherein the second parts of the coverslipper module (30) and the at least one module (32, 34) for handling slides are configured to be disposed in the lower level.

18. The system (10) as recited in claim 1, wherein the transport unit (20) is disposed in the lower level and is operatively connected to the second parts of the coverslipper module (30) and the at least one module (32, 34) for handling slides that extend through the cutouts.

* * * * *